United States Patent [19]

Bessling et al.

[11] Patent Number: 6,028,215
[45] Date of Patent: Feb. 22, 2000

[54] PROCESS FOR PREPARING ESTERS OF CARBOXYLIC ACIDS

[75] Inventors: Bernd Bessling, Grünstadt; Bernd Lohe, Heidelberg; Rüdiger Welker, Dannstadt-Schauernheim; Walter Disteldorf, Wachenheim; Jean Werner Knab, Limburgerhof, all of Germany

[73] Assignee: BASF Aktiengesellschaft, Ludwigshafen, Germany

[21] Appl. No.: 09/109,767

[22] Filed: Jul. 6, 1998

[30] Foreign Application Priority Data

Jul. 4, 1997 [DE] Germany ............... 197 28 683

[51] Int. Cl.⁷ .................................. C07C 67/08
[52] U.S. Cl. ......................................... 560/265
[58] Field of Search ............................. 560/265

[56] References Cited

U.S. PATENT DOCUMENTS 4,314,947 2/1982 Hohenschutz et al. ............ 560/265 X
4,939,294 7/1990 Agreda et al. ..................... 560/265
5,008,046 4/1991 Bremus et al. ..................... 560/265 X

*Primary Examiner*—Michael G. Ambrose
*Attorney, Agent, or Firm*—Keil & Weinkauf

[57] ABSTRACT

A process for preparing esters from alcohol and carboxylic acid by a) feeding a mixture, comprising at least alcohol and/or carboxylic acid as educts, into a distillation column with separated sections containing reactive and conventional internals, wherein the reactive internals are arranged below the inlet of the mixture and conventional internals are arranged above the inlet of the mixture, b) reaction of the alcohol and the carboxylic acid in the reactive internals in presence of a catalyst, c) distillative separation of the evolving reaction mixture into the higher boiling ester and a lower boiling azeotrope containing alcohol, water and ester, wherein the ester accumulates in the bottom and the azeotrope is removed overhead, d) separation of the azeotrope in a phase separator in an aqueous phase and in an organic phase and the organic phase to be returned to the top of the column, wherein in step b) a heterogenous catalyst is utilized and in step c) the ester is taken off above the bottom as pure product between further conventional internals which differ in their arrangement from those in step a) and which are arranged above the inlet of a circulating evaporator.

11 Claims, 1 Drawing Sheet

PROCESS FOR PREPARING ESTERS OF CARBOXYLIC ACIDS

The invention relates to a process for preparing esters from alcohol and carboxylic acid using a catalyst and removing the ester in a rectification column with internals.

Internals in this connection are generally plates, and random and ordered packings. Internals which additionally allow heterogeneous catalysts to be immobilized (see, for example, EP-B1 0 396 650 and EP-B1 0 008 860), or internals whose design provides a holdup time for homogene-ously catalyzed reactions and which are loaded with homogeneous catalysts, are referred to more accurately hereinafter as reactive internals (reaction plates, reactive random and ordered packings). Internals exclusively for distillation purposes are referred to as conventional.

It is known to obtain, for example, butyl acetate by a catalytic esterification of acetic acid with butanol in the liquid phase. In this case, the starting materials are reacted to equilibrium in a reactor. The stream leaving the reactor is fed to a rectification column where the water of esterification is stripped off with the azeotrope of butyl acetate and butanol. The organic phase is separated from the aqueous phase in a phase separator and the organic phase is returned to the column. The chemical equilibrium is changed by the water being evaporated off so that further conversion into butyl acetate takes place on the small number of reaction plates provided. Although in this case the boiling points of the starting materials are between those of the products, because the behavior of the material systems are distinctly nonideal they cannot be kept out of the bottom product simply by distillation measures. The conversion is therefore incomplete and the bottom product contains not only the butyl acetate which is to be isolated but also residues of the starting materials butanol and acetic acid and, where appropriate, an acid catalyst. The acetic acid is neutralized and extracted as salt with water. Excess butanol and remaining water are removed in downstream columns.

From the Journal "Chemie Ingenieur Technik", (Chemie-Ing. Techn., 43., 1971, No. 18, 1001 to 1007) a process for the preparation of esters from alcohol and carboxylic acid is known wherein the esterification is carried out in the reactive internals of a distillation column. In the top section of this distillation column conventional internals are arranged, wherein the reactive internals are arranged below the inlet of the fed mixture. This mixture additionally includes beside the educts a catalyst. It is a homogenous catalyst, preferably sulfuric acid. The latter accumulates in the bottom of the distillation column and is to be returned to the process. The use of the sulfuric acid negatively leads to corrosion of the concerning installations of the plant and to the formation of poisonous sulfate compounds. The ester which accumulates in the bottom of the distillation column together with the sulfuric acid is taken off in the vapor state a short range above the bottom state.

This crude ester contains alcohol as a reminder. The latter is removed in a further distillation column to obtain the pure product.

The problem underlying the present invention was to improve the above mentioned process for the preparation of esters in that, a) to reduce the costs of the plant
b) to employ a heterogenous catalyst to avoid the disadvantages caused by the homogenous catalyst (use of sulfuric acid).

The solution of the problem is based on a process for the preparation of esters by, a) feeding a mixture, comprising at least alcohol and/or carboxylic acid as educts, into a distillation column with separated sections containing reactive and conventional internals, wherein the reactive internals are arranged below the inlet of the mixture and conventional internals are arranged above the inlet of the mixture, b) reaction of the alcohol and the carboxylic acid in the reactive internals in presence of a catalyst, c) distillative separation of the evolving reaction mixture into the higher boiling ester and a lower boiling azeotrope containing alcohol, water and ester, wherein the ester accumulates in the bottom and the azeotrope is removed overhead, d) separation of the azeotrope in a phase separator in an aqueous phase and in an organic phase and the organic phase to be returned to the top of the column, characterized in that, in step b) a heterogenous catalyst is utilized and in step c) the ester is taken off above the bottom as pure product between further conventional internals which differ in their arrangement from those in step a) and which are arranged above the inlet of a circulating evaporator.

According to the invention also a device for carrying out this process is provided which comprises the following installations:

i) a distillation column with reactive and conventional internals
ii) a phase separator
iii) a strip column
iv) a circulating evaporator
v) optionally a prereactor and
the corresponding conductions between the items i) to v).

Numerous possible designs for incorporating heterogeneous catalysts in distillation columns are described in the literature. These include holdup plates where the catalyst can be arranged on the plates or in their downcomers, also coated random packings (TU Clausthal), wound and structured packings with catalyst woven in (Sulzer, Koch, CD Tech).

DETAILED DESCRIPTION OF THE DRAWING

Figure 1:
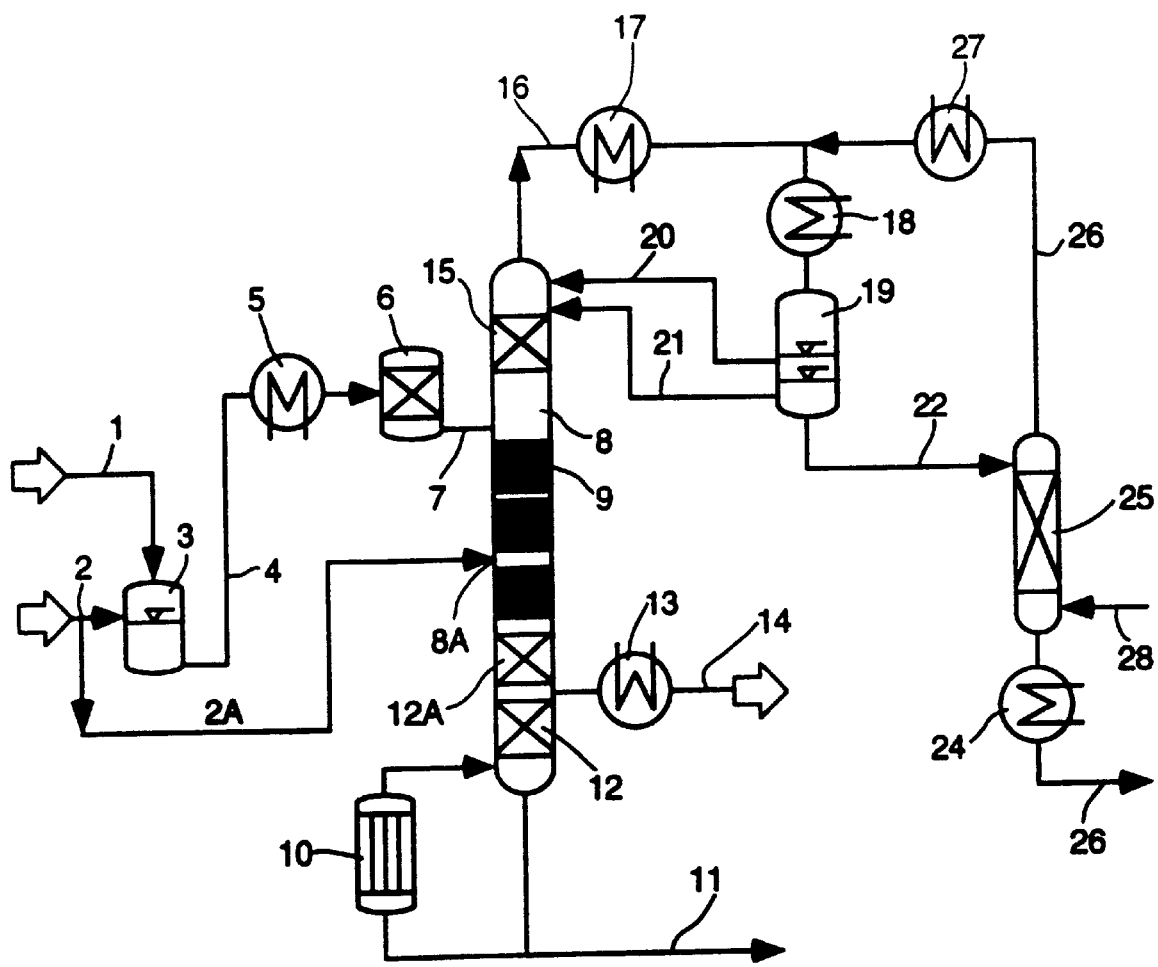
FIG. 1, is a diagrammatic illustration an apparatus which may be used for carrying out this invention in the esterification of acetic acid with butanol. It includes a distillation column (8) with reactive and conventional internals, a phase separator (19), a strip column (25), a circulating evaporator (10), and, optionally, a prereactor (6).

Suitable esterification catalysts are any acidic catalysts ($H^+$ form) such as ion exchange resins (Lewatit® supplied by Bayer). The pressure and thus the reaction temperature may vary depending on the temperature-resistance of the catalysts. The corresponding increase in the reaction rate allows the column to be designed more compactly. The temperatures should be chosen so that the catalyst is not damaged. It is desirable at the same time to keep the condensation temperatures distinctly above ambient temperature. The relationships between concentrations, pressure and temperatures for a given material system are known per se.

For the butyl acetate system, when the thermal exposure limit of the catalyst is, for example, 150° C. the resulting possible pressure range is 300–2000 mbar with temperatures of 50–160° C. inside the column. Operation under atmospheric pressure is to be preferred. The dependence of the reaction rate on the system temperature determines the required catalyst volume.

Deactivation of the incorporated catalyst, eg. by foreign ions, can be reduced by an upstream guard bed. This bed contains the heterogeneous catalysts also employed in the distillation column. The advantage of such a bed is that it can be exchanged relatively easily after deactivation of its catalyst during operation, especially when it is possible to switch to a parallel replacement guard bed. This results in a quite considerable increase in the operating life of the complete system. This bed can also be extended to be a complete prereactor, which reduces the reaction volume in the column.

In an advantageous embodiment of the invention, the rectification column can advantageously be divided into regions which may have various types of conventional or reactive internals.

The feeds can in principle take place at different points so that the more volatile precursor is added in the lower part, and the less volatile in the upper part, of the rectification column. The precursors then flow counter-currently through the column. This results in a change of the esterification equilibrium at the individual reaction stages. This makes it possible to increase the space-time yield in the individual stages and thus to reduce the catalyst volume required in the complete rectification column. However, if the boiling points of the precursors are close together, it is generally sufficient to have a common feed of the specific mixture of substances. As a rule, the reactive internals are arranged between the precursor feed and the target ester takeoff. It is possible for conventional internals (without catalyst) to be incorporated in the distillation column above and below this. However, it may be advantageous for the reaction zone also to be extended to the region above the feed by arranging reactive internals above the latter.

In the reactive distillation according to the invention, the number of reaction stages is chosen so that the initial acid can be removed during the esterification. It is possible by accurately matching the number of plates and the reaction volume to optimize the two precursors appropriate for complete conversion, and an ester complying with specifications can be taken off. If the parameters are known, this is routine for the skilled worker. In the case of the preparation of butyl acetate, it was possible to isolate the latter with a purity of 99.9% by weight and a residual acid content of 50 ppm.

Further details and advantages of the invention can be inferred from the example described in the drawing for the preparation of n-butyl acetate from n-butanol and acetic acid.

Acetic acid is fed through line 1 and part of the amount of butanol necessary for the required reaction is fed through line 2 into a mixing tank 3. The remaining part of the butanol necessary for the reaction is fed through line 2a directly to the column 8 at point 8a. The precursor mixture produced in the tank 3 is introduced from there through line 4 and through a heat exchanger 5 into a guard bed 6. This guard bed can also be designed as prereactor. It contains a defined amount of the catalyst necessary for the subsequent reaction. This guard bed serves to reduce the deactivation of the catalyst incorporated in the column, which makes it possible to achieve a considerably longer service life of this catalyst. The guard bed can be designed to be relatively small. The reaction mixture is passed from the guard bed 6 through line 7 into the column 8 which operates under a pressure of about 1 bar and in which the actual reaction takes place.

This column 8 is provided according to the invention with reactive internals 9 which are provided with the catalyst necessary for the reaction. These internals 9 can be, in a manner known per se, holdup plates on which, or in whose downcomers, the catalyst is arranged. Other possibilities are coated random packings, wound or structured packings with catalyst woven in and the like. 40 such stages are provided in one example. In the example depicted, they are shown in three sections. The bottom of the column 8 is heated by a circulating evaporator 10. Residue is taken off through line 11. The packings 12 and 12a arranged above the inlet of the circulating evaporator 10 contain no catalyst. The product n-butyl acetate to be isolated is taken off in a purity of 99.9% by weight above the packing 12 through line 14 and through a heat exchanger 13.

It is likewise possible to arrange a conventional packing 15 above the feed line 7 into the column 8. Above this packing 15, the water produced in the reaction flows as azeotropic mixture of water, butanol and butyl acetate through line 16 and through a heat exchanger 17 into a phase separator 19. Separated organic liquid flows from the latter through line 20 back to the top of the column 8. It is also possible for parts of the water of esterification removed in the phase separator 19 to be returned through line 21 to the top of the column 8. Part of the water is taken off at the lower end of the phase separator 19 through line 22. This part of the aqueous phase in the phase separator 19 still contains organic substances. It can therefore also be advantageously worked up. This is done in a small stripping column 25, into the top of which this water is fed through line 22. Steam is fed through line 23 into the bottom of this stripping column 25. A small amount of slightly polluted waste water is discharged through a heat exchanger 24 and through line 26 from the bottom of the stripping column. Steam taken off from the top of this stripping column 25 is returned through line 28 and heat exchanger 27 to the phase separator 19.

In the example, the column is operated under atmospheric pressure. The distillate and bottom temperatures correspond to the boiling points of the low-boiler azeotrope and of butyl acetate respectively.

Other esters can also be prepared according to the invention in a manner corresponding to the process described above, such as alkyl acetates, glycol ether acetates and the like.

The esterification of n-butanol with acetic acid by the reactive distillation according to the invention is explained in detail by means of a specific example below, and is depicted diagrammatically in the drawing.

In the example, the column 8 was a laboratory column with a diameter of 0.055 m. The concentrating part and stripping part (below the reaction zone) were each composed of four 0.5 m packing sections at 300 m$^2$/m$^3$. The part in which the reaction takes place was formed by a catalyst packing with an esterification catalyst (ion exchanger, detoxane) (Lewatit 2631, Bayer), separated into 7 packing segments each of 1 m and each with collectors and distributors. The content of catalyst with respect to the free colume of column is 10%–50% by volume in the reaction zone. The butanol feed (1–1.2 kg/h) was distributed in the ratio 1:2 to two points above and in the middle of the reaction zone. Tests were carried out with variation of this ratio and the position of this middle feed point 8A. Water, butanol and butyl acetate were taken off as vapor through line 16 above the second section 9. Water with dissolved butanol (about 6% by weight) was taken off from the decanter 19, and the organic phase was all returned through line 20 to the column 8. About 10 g/h bottom product (high boilers) were discharged through line 11.

The system was operated at from 300 to 2000 mbar. The pressure drop was 25 mbar, mainly in the reactive part.

At 700 mbar, the bottom temperature was 112.1° C. and the distillate temperature corresponded to the ternary azeotrope at 81° C. The azeotrope composition was about 12% n-butanol, 70% butyl acetate and 18% water (% by weight). Directly below the reaction zone the acetic acid concentration had been reduced to about 300 ppm, while there was still about 5% by weight n-butanol present.

The energy input was about 200 kW/to butyl acetate. The process was not sensitive to the heat input.

In the tests, butyl acetate was obtained with only 300 ppm residual acetic acid; this corresponds to a conversion of 99.95%. The water measurement showed <40 ppm. Also present were small amounts of butanol and by-products (ethers). With less stringent specifications for the products, the reaction and separation zones can be distinctly shorter.

Conversion of the laboratory column to the industrial scale is known to the skilled worker.

We claim:

1. A process for preparing esters from alcohol and carboxylic acid by
   a) feeding the alcohol, the carboxylic acid, or an admixture thereof as educt into a distillation column with separated sections containing reactive and conventional internals, wherein the reactive internals are arranged below the inlet of the said educt and conventional internals are arranged above the said inlet,
   b) reacting the alcohol and the carboxylic acid in the reactive internals in presence of a catalyst,
   c) distillatively separating the evolving reaction mixture into the higher boiling ester and a lower boiling azeotrope containing alcohol, water and ester, wherein the ester accumulates in the bottom and the azeotrope is removed overhead,
   d) separating the azeotrope in a phase separator into an aqueous phase and in an organic phase and the organic phase is returned to the top of the column,
      wherein, in step b) a heterogeneous catalyst is utilized and in step c) the ester is taken off above the bottom as pure product between further conventional internals which differ in their arrangement from those in step a) and which are arranged above the inlet of a circulating evaporator.

2. A process according to claim 1, characterized in that, in sections with reactive internals the content of heterogenous catalyst is 10 to 50 volume-% by the volume of the column.

3. A process according to claim 1, characterized in that, as heterogenous catalyst an ion exchanger is used.

4. A process according to claim 1, characterized in that, the pressure of the distillation column is 300 mbar to 2000 mbar.

5. A process according to claim 1, characterized in that, the temperature in the distillation column is 50° C. to 160° C.

6. The process of claim 1 wherein the alcohol is butanol and the carboxylic acid is acetic acid.

7. The process of claim 1 where the educt is a mixture comprising essentially all of said alcohol and said acid in step a).

8. The process of claim 1 wherein, in step a), a mixture of said alcohol and said acid is passed through a prereactor containing the same heterogeneous catalyst employed in the distillation column.

9. The process of claim 1 wherein, in step a), at least part of the lower boiling of said alcohol or of said carboxylic acid is first fed separately into and inlet of the distillation column at a position below said inlet for said educt and below at least one of said reactive internals.

10. The process of claim 6 wherein essentially all of the said alcohol and all of the said carboxylic acid are separately fed in the distillation column.

11. The process of claim 4 wherein the pressure of the distillation column is essentially atmospheric pressure.

* * * * *